United States Patent
Nagamatsu et al.

[11] Patent Number: 5,990,118
[45] Date of Patent: Nov. 23, 1999

[54] PURINE COMPOUNDS AND XANTHINE OXIDASE INHIBITORS

[75] Inventors: Tomohisa Nagamatsu, Okayama; Yoko Watanabe, Choshi; Kazuki Endo, Choshi; Masahiro Imaizumi, Choshi, all of Japan

[73] Assignee: Yamasa Corporation, Chiba, Japan

[21] Appl. No.: 08/894,474

[22] PCT Filed: Feb. 21, 1996

[86] PCT No.: PCT/JP96/00391

§ 371 Date: Aug. 20, 1997

§ 102(e) Date: Aug. 20, 1997

[87] PCT Pub. No.: WO96/26208

PCT Pub. Date: Aug. 29, 1996

[30] Foreign Application Priority Data

Feb. 21, 1995 [JP] Japan ......................................... 7-56536
Feb. 21, 1995 [JP] Japan ......................................... 7-056537
Feb. 27, 1995 [JP] Japan ......................................... 7-063377
Feb. 27, 1995 [JP] Japan ......................................... 7-063378
Sep. 1, 1995 [JP] Japan ......................................... 7-248739
Sep. 1, 1995 [JP] Japan ......................................... 7-248740

[51] Int. Cl.$^6$ ..................... A61K 31/52; C07D 473/34; C07D 487/14
[52] U.S. Cl. ..................... 514/261; 514/262; 514/267; 544/251; 544/265; 544/276; 544/277
[58] Field of Search ..................... 544/251, 265, 544/276; 514/261, 262, 267

[56] References Cited

PUBLICATIONS

A. Griner–Sorolla et al., "Nitrosaminopurines and Nucleosides, Synthesis and Biological Activivty", *Journal of Medicinal Chemistry*, vol. 16, No. 4, pp. 365–369 (1973).

J. Goodfellow, "Cooperative Effects in Water–biomolecule Crystal Systems", *Proc. Natl. Acad. Sci.* USA, vol. 79, pp. 4977–4979 (Aug. 1982).

Brown et al., Aust. Chem35(6), 1263–7, 1982.

*Primary Examiner*—Phyllis G. Spivack
*Attorney, Agent, or Firm*—Wenderoth, Lind & Ponack, L.L.P.

[57] ABSTRACT

Purine or triazolopurine compounds are disclosed represented by formula (I) or (II):

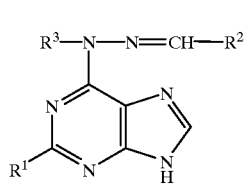

(I)

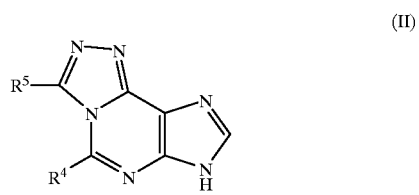

(II)

wherein $R^1$ and $R^4$ represent each hydrogen, halogeno, hydroxy, mercapto, or amino; $R^2$ represents alkyl or aryl; and $R^3$ and $R^5$ represent each hydrogen, alkyl, or aryl; and pharmaceutical compositions comprising these compounds as xanthine oxidase inhibitors, remedies for hyperuricemia, or remedies or preventive agents for gout.

17 Claims, No Drawings

PURINE COMPOUNDS AND XANTHINE OXIDASE INHIBITORS

This application is a 371 of PCT/JP96/00391 filed Feb. 21, 1996.

TECHNICAL FIELD

The present invention relates to novel purine compounds or triazolopurine compounds having xanthine oxidase inhibitory activity, as well as to pharmaceutical compositions containing the compounds as an active ingredient.

BACKGROUND ART

Xanthine oxidase is an enzyme which plays an important role in in vivo uricogenesis. Thus, xanthine oxidase inhibitors are useful as remedies for hyperuricemia, which is a causal disease of gouty attack, and as preventive agents against gouty attack. Presently, allopurinol is the sole drug clinically used as a xanthine oxidase inhibitor. Compounds other than allopurinol having xanthine oxidase inhibitory activity have been reported, and some of them are under investigation for the development of pharmaceuticals (Japanese Patent Application Laid-Open (kokai) Nos. 5-310742 and 6-316578, and Japanese Patent Publication (kokoku) No. 6-41466).

Recently, purines have been reported to have pharmacological activities such as bronchodialating action, and therefore, use of the compounds as pharmaceuticals is expected [Pharmaceutical Society of Japan, Lecture Summaries of the 112th Annual Conference, 233 (1992)]. However, xanthine oxidase inhibitory activities of those compounds have so far not been reported.

Accordingly, the primary object of the present invention is to provide novel purine compounds endowed with xanthine oxidase inhibitory activity.

DISCLOSURE OF THE INVENTION

The present inventors have conducted careful studies in an attempt to attain the above-mentioned object, and have found that purine compounds or triazolopurine compounds having a specific structure exhibit a xanthine oxidase inhibiting effect and are useful as pharmaceuticals. The present invention was accomplished based on this finding.

Accordingly, the present invention is directed to a purine compound of the following formula (I):

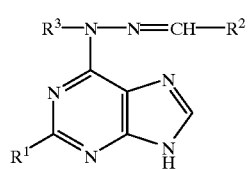

(I)

(wherein $R^1$ represents a hydrogen atom, a halogen atom, a hydroxyl group, a mercapto group, or an amino group; $R^2$ represents an alkyl group or an aryl group; and $R^3$ represents a hydrogen atom, an alkyl group, or an aryl group), as well as to pharmaceutical compositions containing the compound as an active ingredient, such as xanthine oxidase inhibitors, remedies for hyperuricemia, and preventive and therapeutic agents for gout.

The present invention is also directed to a triazolopurine compound of the following formula (II):

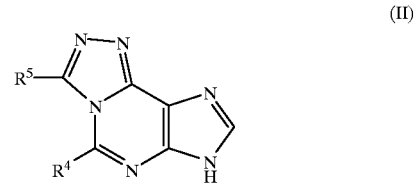

(II)

(wherein $R^4$ represents a hydrogen atom, a halogen atom, a hydroxyl group, a mercapto group, or an amino group; and $R^5$ represents a hydrogen atom, an alkyl group, or an aryl group), as well as to pharmaceutical compositions containing the compound as an active ingredient, such as xanthine oxidase inhibitors, remedies for hyperuricemia, and preventive and therapeutic agents for gout.

The present invention is also directed to use of the above-described purine compound of formula (I) or triazolopurine compound of formula (II) as a xanthine oxidase inhibitor, a remedy for hyperuricemia, or as a preventive and therapeutic agent for gout.

The present invention is also directed to a method for preventing and treating hyperuricemia or gout, characterized by administering an effective amount of the aforementioned purine compound (I) or triazolopurine compound (II).

BEST MODES FOR CARRYING OUT THE INVENTION

The purine compounds of the present invention are represented by the above-described formula (I), and $R^1$ to $R^3$ in the formula are defined as above.

The halogen atoms represented by $R^1$ include a chlorine atom, a bromine atom, an iodine atom, and a fluorine atom.

The alkyl groups represented by $R^2$ and $R^3$ include C1–C7 linear or branched lower alkyl groups such as methyl, ethyl, propyl, and butyl.

The aryl groups represented by $R^2$ and $R^3$ include a phenyl group having a substituent of the following formula (III):

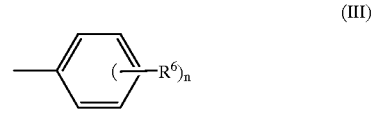

(III)

(wherein $R^6$ represents a halogen atom, an alkyl group, an alkoxy group, an amino group, an alkylamino group, a methylenedioxy group, a hydroxyl group, or a nitro group; and the number of substituent, n, represents an integer between 1 and 5 inclusive), and a phenyl group. In the present specification, the number and position of the substituent represented by $R^6$ are not particularly limited.

Specific examples of such aryl groups include a phenyl group; an alkylphenyl group having 1 to 5 carbon atoms, such as methylphenyl or ethylphenyl; an alkoxyphenyl group having 1 to 5 carbon atoms such as methoxyphenyl or ethoxyphenyl; an alkylaminophenyl group having 1 to 5 carbon atoms such as dimethylaminophenyl or diethylaminophenyl; a halogenophenyl group such as chlorophenyl, bromophenyl, fluorophenyl, or iodophenyl; methylenedioxyphenyl; hydroxyphenyl; and nitrophenyl.

Of the purine compounds of formula (I) according to the present invention, preferred compounds satisfy at least one of the following criteria:

1) $R^1$ is a hydroxyl group,
2) $R^1$ is a mercapto group,
3) $R^2$ is an aryl group,
4) $R^2$ is an alkyl group,
5) $R^3$ is an aryl group,
6) the compound is in a free form,
7) the compound is in the form of a salt.

More preferred compounds satisfy the following criteria:
(1) $R^1$ is a hydroxyl group, $R^2$ is an aryl group, and $R^3$ is an alkyl group,
(2) $R^1$ is a mercapto group, $R^2$ is an aryl group, and $R^3$ is an alkyl group,
(3) $R^1$ is a hydroxyl group, $R^2$ is an aryl group, and $R^3$ is an aryl group,
(4) $R^1$ is a mercapto group, $R^2$ is an aryl group, and $R^3$ is an aryl group.

The method for the preparation of the purine compound of formula (I) of the present invention is not particularly limited, and a compound of formula (I) in which $R^3$ is a hydrogen atom may be prepared, for example, in accordance with the following reaction scheme:

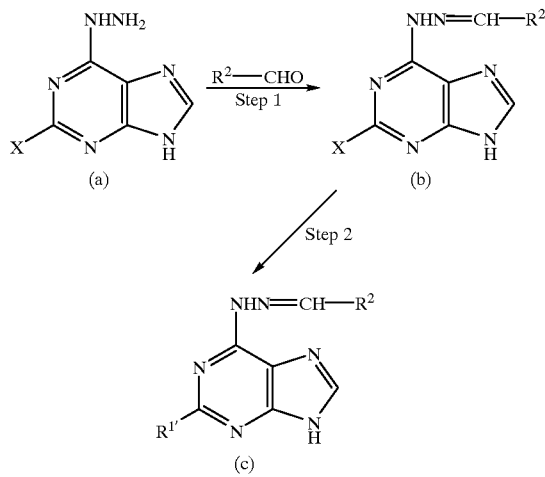

(wherein X represents a halogen atom, a hydroxyl group, a mercapto group, or an amino group; $R^{1'}$ represents a hydrogen atom, a hydroxyl group, a mercapto group, or an amino group, and $R^2$ has the same meaning as defined above).

Briefly, a compound of formula (a) is reacted with an aldehyde to obtain a compound of formula (b) (Step 1). In the case in which X is a halogen atom, catalytic hydrogenation of compound (b) or treatment of compound (b) with potassium hydroxide, thiourea, or liquid ammonium provides a compound (c) in which $R^{1'}$ is a hydrogen atom, a hydroxyl group, a mercapto group, or an amino group, respectively (Step 2). Each step will next be described hereinbelow.

(Step 1)

Compound (a), the starting material, is either a known compound (J. Am. Chem. Soc., 79, 2185 (1957)) or a compound that can be easily prepared from a known compound. One mole of compound (a) is reacted with 1-2 moles of an aldehyde represented by $R^2$—CHO (wherein $R^2$ has the same meaning as defined above) for 1–30 hours at 10–40° C. in an organic solvent such as dioxane or acetic acid to obtain compound (b).

(Step 2)

Among compounds (b), compounds in which X is a halogen atom may be subjected, for example, to the following process so as to synthesize a compound (c) in which X is not a halogen atom.

Briefly, compounds (c) in which $R^{1'}$ is a hydrogen atom may be synthesized through catalytic hydrogenation of a compound (b), in which X is a halogen atom, in ethanol or acetonitrile in a stream of hydrogen by use of a palladium catalyst.

Compounds (c) in which $R^{1'}$ is a hydroxyl group may be synthesized by reacting 1 mmole of a compound (b) in which X is a halogen atom with 1–30 ml of 5% aqueous KOH solution for 1–10 hours at 50–100° C.

Compounds (c) in which $R^{1'}$ is a mercapto group may be synthesized by reacting 1 mole of a compound (b) in which X is a halogen atom with 1–4 times by mole of thiourea in an organic solvent such as ethanol for 1–20 hours at a temperature between 80° C. and a reflux temperature.

Compounds (c) in which $R^{1'}$ is an amino group may be synthesized by reacting 1 mmole of a compound (b) in which X is a halogen atom with 1–40 ml of liquid ammonia in a sealed tube for 1–6 hours at 80–120° C.

Next, among the purine compounds (I) of the present invention, compounds in which $R^3$ is an alkyl or aryl may be synthesized, for example, in accordance with the following reaction scheme:

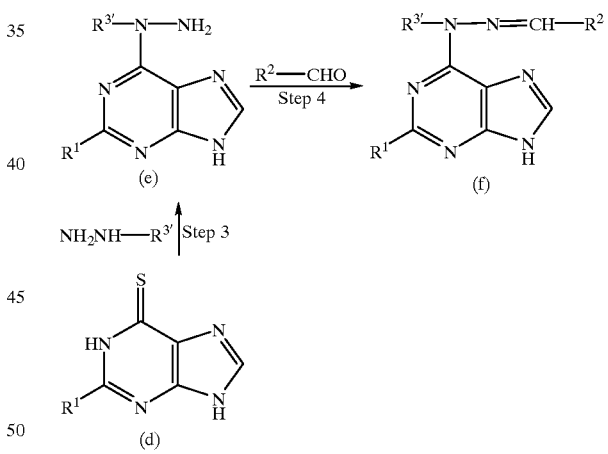

(wherein $R^{3'}$ represents an alkyl group or an aryl group, and $R^1$ and $R^2$ have the same meanings as defined above).

Briefly, a compound represented by formula (d) is reacted with a hydrazine to provide a compound of formula (e) (Step 3), and subsequently, the resultant compound (e) is reacted with an aldehyde to obtain a compound of formula (f) (Step 4). Each step will next be described hereinbelow.

(Step 3)

Compound (d), the starting material, is either a known compound (J. Am. Chem. Soc., 76, 5633 (1954)) or a compound that can be easily prepared from a known compound.

One mole of compound (d) is reacted with 50–70 moles of a hydrazine represented by $NH_2NH$—$R^{3'}$ (wherein $R^{3'}$ has the same meaning as defined above) in a sealed tube for 20–40 minutes at 100–150° C. to obtain compound (e). (Step 4)

One mole of compound (e) is reacted with 1–2 moles of an aldehyde represented by $R^2$—CHO (wherein $R^2$ has the same meaning as defined above) for 2–6 hours at 10–40° C. in an organic solvent such as dioxane or acetic acid to obtain compound (f).

The triazolopurine compounds of the present invention are represented by formula (II), and $R^4$ and $R^5$ in the formula are as defined above.

The halogen atoms represented by $R^4$ are the same as those listed for the halogen atoms of $R^1$ described hereinabove.

The alkyl groups represented by $R^5$ are the same as those listed for the alkyl groups of $R^2$ or $R^3$ described hereinabove.

The aryl groups represented by $R^5$ are the same as those listed for the aryl groups of $R^2$ or $R^3$ described hereinabove.

Of the triazolopurine compounds of formula (II) according to the present invention, preferred compounds satisfy at least one of the following criteria:

1) $R^4$ is a hydroxyl group,
2) $R^4$ is a mercapto group,
3) $R^5$ is an aryl group,
4) the compound is in a free form,
5) the compound is in the form of a salt.

More preferred compounds satisfy the following criteria:

(1) $R^4$ is a hydroxyl group, and $R^5$ is an aryl group.

The method for the preparation of the triazolopurine compound of formula (II) of the present invention is not particularly limited, and may be prepared, for example, in accordance with the following reaction scheme:

oxidizing agent to yield a compound of formula (g) (Step 5). In the case in which X is a halogen atom, catalytic hydrogenation of compound (g) or treatment of compound (g) with thiourea provides a compound (h) in which $R^{4'}$ is a hydrogen atom or a mercapto group, respectively (Step 7). Alternatively, the compound of formula (g) may also be obtained through reaction of a formula (a) compound and an orthoester (Step 6). Each step will next be described hereinbelow.

(Step 1')

In the case in which $R^5$ of the target compound is not a hydrogen atom but is an alkyl group or aryl group, 1 mole of compound (a) is reacted with 1–2 moles of an aldehyde represented by $R^{5'}$—CHO (wherein $R^{5'}$ is an alkyl group or aryl group) for 1–10 hours at 10–40° C. in an organic solvent such as dioxane to obtain compound (b').

(Step 5)

One mole of compound (b') is reacted with 1–4 moles of an oxidizing agent such as diethylazodicarboxylate or lead tetraacetate in an organic solvent such as dioxane for 1–10 hours at 10–150° C. to obtain compound (g).

(Step 6)

In the case in which $R^5$ of the target compound is a hydrogen atom, a methyl group, or a phenyl group, 1 mmole of compound (a) is reacted with 1–20 mmoles of an orthoester such as triethyl orthoformate, triethyl orthoacetate, or triethylorthobenzoate, in the presence of trifluoroacetic acid if required, for 1–10 hours at 10–180° C. to obtain compound (g).

(Step 7)

Among compounds (g), compounds in which X is a halogen atom may be transformed into compounds (h) by, for example, the following process of synthesis.

Briefly, compounds (h) in which $R^{4'}$ is a hydrogen atom may be synthesized through catalytic hydrogenation of a

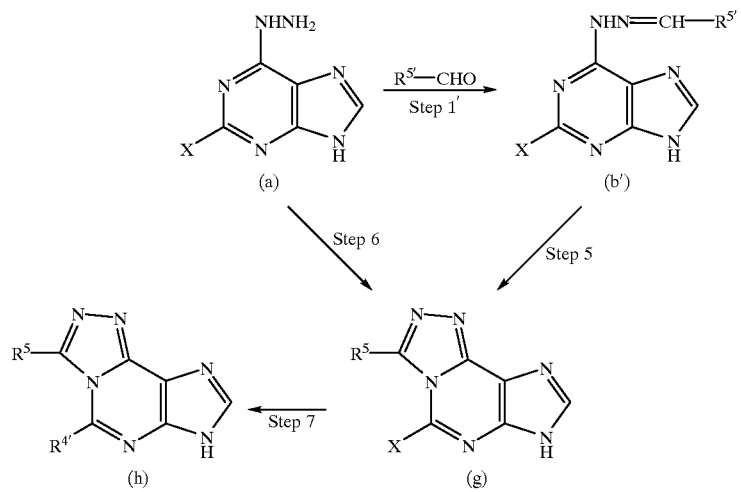

(wherein X represents a halogen atom, a hydroxyl group, a mercapto group, or an amino group; $R^{4'}$ represents a hydrogen atom, a hydroxyl group, a mercapto group, or an amino group, and $R^{5'}$ represents an alkyl group or an aryl group, and $R^5$ has the same meaning as defined above).

Briefly, a compound of formula (a) is reacted with an aldehyde to obtain a compound of formula (b') (Step 1'). Subsequently, compound (b') is cyclized by use of an compound (g) in which X is a halogen atom in ethanol or acetonitrile in a stream of hydrogen by use of a palladium catalyst.

Compounds (h) in which $R^{4'}$ is a mercapto group may be synthesized by reacting 1 mmole of compound (g) in which X is a halogen atom with 1–4 times by mole of thiourea in an organic solvent such as ethanol for 2–20 hours at a temperature between 80° C. and a reflux temperature.

The compounds of formulas (I) and (II) of the present invention as well as synthesic intermediates may be separated and purified by customary means used for separating and purifying nucleotides. For example, recrystallization and a variety of chromatography may be used.

The purine compounds (I) or triazolopurine compounds (II) of the present invention may be in a free form, salt form, or hydrate (including salt hydrate) form. For example, compounds of a salt type include inorganic acid salts such as hydrochlorides, sulfates, and hydrobromides; organic acid salts such as oxalates, citrates, and malates; or ammonium salts. Particularly, pharmaceutically acceptable salts are preferred.

In the case in which $R^1$ or $R^4$ is an amino group, a hydroxyl group, or a mercapto group, the purine compounds (I) or triazolopurine compounds (II) may exist as tautomers such as imino type, oxo type, or thioxo type compounds.

The purine compounds and triazolopurine compounds of the present invention exhibit a xanthine oxidase inhibiting effect, and thus are useful as remedies for hyperuricemia, and as preventive and therapeutic agents for gout. The compounds may be administered to a subject in need of prevention or treatment of hyperuricemia by oral administration, enteric administration, parenteral administration, or topical administration. The dose is determined in accordance with the age, pathological condition, body weight, etc. of the patient. Usually, the dose is determined within the range of between 0.01 and 1,000 mg/kg, and is administered a single time or is divided among a plurality of times.

When the compounds of the present invention are used as pharmaceuticals, the compounds are preferably formed into compositions containing pharmacologically acceptable carriers such as vehicles and other additives. Examples of carriers include solid carriers such as lactose, kaolin, sucrose, crystalline cellulose, cornstarch, talc, agar, pectin, stearic acid, magnesium stearate, lecithin, and sodium chloride; and liquid carriers such as glycerol, peanut oil, polyvinylpyrrolidone, olive oil, ethanol, benzyl alcohol, propylene glycol, and water.

The physical form, i.e., dosage form, of the pharmaceutical compositions is determined arbitrarily. For example, when solid carriers are incorporated, tablets, powders, granules, capsules, suppositories, and lozenges may be formed, and when liquid carriers are incorporated, syrups, emulsions, soft gelatin capsules, creams, gels, pastes, and injections may be formed.

EXAMPLES

The present invention will be described more specifically by way of examples, which should not be construed as limiting the invention.

(Synthesis examples of purine compounds)

Purine compounds of 3a through 3i were synthesized in accordance with the following reaction scheme:

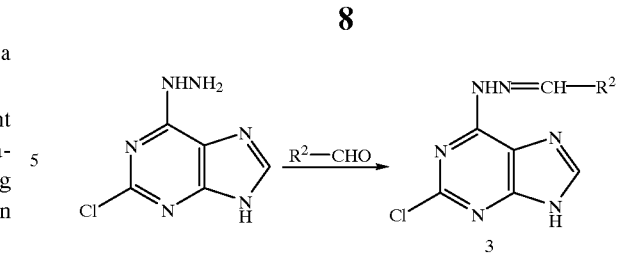

(wherein $R^2$ has the same meaning as defined above).

Synthesis Example 1
Synthesis of 2-chloro-6-n-butylidenehydrazino-9H-purine [3a: $R^2$=n-propyl]

2-Chloro-6-hydrazino-9H-purine (1.0 g, 5.4 mmol) and butyl aldehyde (0.58 g, 8.1 mmol) were added to dioxane (40 ml), and the mixture was stirred for 10 hours at room temperature. After completion of reaction, the solvent was evaporated under reduced pressure so as to precipitate solid crystals. The crystals were recrystallized from ethanol to obtain 0.9 g (yield 70%) of colorless powdery crystals (m.p.>300° C.).

Synthesis Example 2
Synthesis of 6-benzylidenehydrazino-2-chloro-9H-purine [3b: $R^2$=phenyl]

2-Chloro-6-hydrazino-9H-purine (1.0 g, 5.4 mmol) and benzaldehyde (0.69 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from N,N-dimethylformamide (DMF) to obtain 1.27 g (yield 86%) of colorless powdery crystals (m.p.>300° C.).

Synthesis Example 3
Synthesis of 2-chloro-6-p-fluorobenzylidenehydrazino-9H-purine [3c: $R^2$=4-fluorophenyl]

2-Chloro-6-hydrazino-9H-purine (1.0 g, 5.4 mmol) and p-fluorobenzaldehyde (0.81 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from DMF to obtain 1.42 g (yield 90%) of colorless powdery crystals (m.p.>300° C.).

Synthesis Example 4
Synthesis of 2-chloro-6-p-chlorobenzylidenehydrazino-9H-purine [3d: $R^2$=4-chlorophenyl]

2-Chloro-6-hydrazino-9H-purine (1.0 g, 5.4 mmol) and p-chlorobenzaldehyde (0.92 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from DMF to obtain 1.15 g (yield 69%) of colorless powdery crystals (m.p.>300° C.).

Synthesis Example 5
Synthesis of 2-chloro-6-p-methoxybenzylidenehydrazino-9H-purine [3e: $R^2$=4-methoxyphenyl]

2-Chloro-6-hydrazino-9H-purine (1.0 g, 5.4 mmol) and p-anisaldehyde (0.89 g, 6.5 mmol) were added to dioxane (40 ml), and the mixture was stirred for 4 hours at room temperature. After completion of reaction, the solvent was evaporated under reduced pressure so as to precipitate solid crystals. The crystals were recrystallized from DMF to obtain 1.46 g (yield 89%) of colorless powdery crystals (m.p.>300° C.).

Synthesis Example 6

Synthesis of 2-chloro-6-p-N,N-dimethylaminobenzylidenehydrazino-9H-purine [3f: $R^2$=4-dimethylaminophenyl]

2-Chloro-6-hydrazino-9H-purine (1.0 g, 5.4 mmol) and p-dimethylaminobenzaldehyde (0.97 g, 6.5 mmol) were added to dioxane (40 ml), and the mixture was stirred for 3 hours at room temperature. After completion of reaction, the solvent was evaporated under reduced pressure so as to precipitate solid crystals. The crystals were recrystallized from DMF to obtain 1.35 g (yield 79%) of orange-colored powdery crystals (m.p.>300° C.).

Synthesis Example 7

Synthesis of 2-chloro-6-(3,4-methylenedioxybenzylidenehydrazino)-9H-purine [3g: $R^2$=3,4-methylenedioxyphenyl]

2-Chloro-6-hydrazino-9H-purine (1.0 g, 5.4 mmol) and piperonal (0.96 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from DMF to obtain 1.39 g (yield 81%) of colorless needles (m.p.>300° C.).

Synthesis Example 8

Synthesis of 2-chloro-6-p-nitrobenzylidenehydrazino-9H-purine [3h: $R^2$=4-nitrophenyl]

2-Chloro-6-hydrazino-9H-purine (1.0 g, 5.4 mmol) and p-nitrobenzaldehyde (0.98 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from DMF to obtain 1.51 g (yield 88%) of yellow powdery crystals (m.p.>300° C.).

Synthesis Example 9

Synthesis of 2-chloro-6-p-hydroxybenzylidenehydrazino-9H-purine [3i: $R^2$=4-hydroxyphenyl]

2-Chloro-6-hydrazino-9H-purine (1.0 g, 5.4 mmol) and p-hydroxybenzaldehyde (0.79 g, 6.5 mmol) were added to dioxane (40 ml), and the mixture was stirred for 5 hours at room temperature. After completion of reaction, the solvent was evaporated under reduced pressure so as to precipitate solid crystals. The crystals were recrystallized from DMF to obtain 1.36 g (yield 87%) of colorless powdery crystals (m.p.>300° C.).

Purine compound 7 was synthesized in accordance with the following reaction scheme:

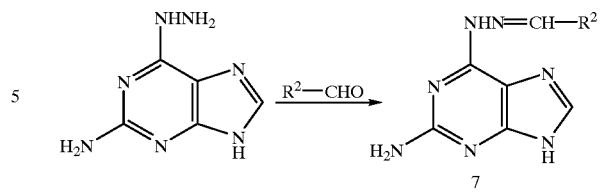

(wherein $R^2$ has the same meaning as defined above).

Synthesis Example 10

Synthesis of 2-amino-6-p-methoxybenzylidenehydrazino-9H-purine [7: $R^2$=4-methoxyphenyl]

2-Amino-6-hydrazino-9H-purine (1.0 g, 6.1 mmol) and p-anisaldehyde (1.24 g, 9.1 mmol) were added to acetic acid (40 ml), and the mixture was stirred for 4 hours at room temperature. After completion of reaction, the solvent was evaporated under reduced pressure so as to precipitate solid crystals. The crystals were recrystallized from DMF to obtain 1.13 g (yield 66%) of colorless powdery crystals (m.p.=174° C. (decomposed)).

$^1$H-NMR (60 MHz, DMSO-d$_6$) δ: 3.82 (3H, s, OMe), 5.86 (2H, br s, exchangeable with D$_2$O, NH$_2$), 7.00 (2H, d, $J_{AB}$=8.76 Hz, Ar-mH), 7.75 (2H, d, $J_{AB}$=8.76 Hz, Ar-oH), 7.90 (1H, s, 8-H), 8.22 (1H, s, N=CH), 11.30 (2H, br, exchangeable with D$_2$O, NH×2)

The purine compounds of 10a through 10g were synthesized in accordance with the following reaction scheme:

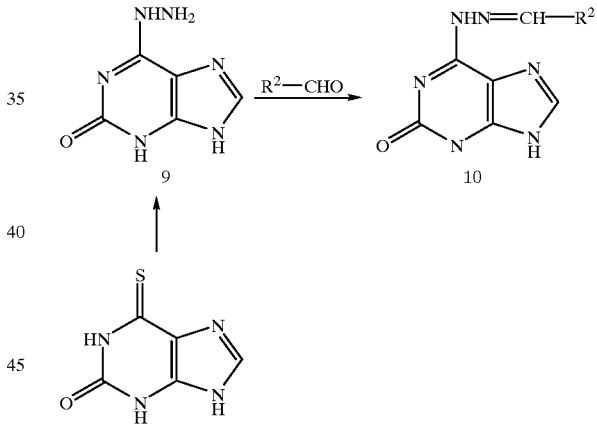

(wherein $R^2$ has the same meaning as defined above).

Synthesis Example 11

Synthesis of 6-p-fluorobenzylidenehydrazino-9H-purine-2 (3H)-one [10a: $R^2$=4-fluorophenyl]

(1) Synthesis of 6-hydrazino-9H-purine-2(3H)-one [9]

2-Oxo-6-thioxo-1,2,3,6-tetrahydro-9H-purine (J. Am. Chem. Soc., 76, 5633 (1954)) (0.5 g, 2.97 mmol) was added to 80% hydrazine hydrate (5 ml), and the mixture was stirred for 10 minutes at 120° C. After completion of reaction, crystals that precipitated were collected by filtration, and washed with water. The crystals were recrystallized from water to obtain 0.31 g (yield 63%) of colorless powdery crystals (m.p.=278° C. (decomposed)).

$^1$H-NMR (60 MHz, DMSO-d$_6$ and D$_2$O) δ: 7.74 (1H, s, 8-H)

(2) Synthesis of 6-p-fluorobenzylidenehydrazino-9H-purine-2(3H)-one [10a: $R^2$=4-fluorophenyl]

6-Hydrazino-9H-purine-2(3H)-one [9] (0.5 g, 3.0 mmol) and p-fluorobenzaldehyde (0.56 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.63 g (yield 77%) of colorless powdery crystals (m.p.=275° C. (decomposed)).

Synthesis Example 12
Synthesis of 6-p-N,N-dimethylaminobenzylidenehydrazino-9H-purine-2(3H)-one [10b: $R^2$=4-dimethylaminophenyl]

6-Hydrazino-9H-purine-2(3H)-one [9] (0.5 g, 3.0 mmol) and p-dimethylaminobenzaldehyde (0.67 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.62 g (yield 69%) of yellow powdery crystals (m.p.=284° C. (decomposed)).

Synthesis Example 13
Synthesis of 6-p-nitrobenzylidenehydrazino-9H-purine-2(3H)-one [10c: $R^2$=4-nitrophenyl]

6-Hydrazino-9H-purine-2(3H)-one [9] (0.5 g, 3.0 mmol) and p-nitrobenzaldehyde (0.68 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.63 g (yield 70%) of yellow powdery crystals (m.p.>300° C.).

Synthesis Example 14
Synthesis of 6-p-methoxybenzylidenehydrazino-9H-purine-2(3H)-one [10d: $R^2$=4-methoxyphenyl]

6-Hydrazino-9H-purine-2(3H)-one [9] (0.5 g, 3.0 mmol) and p-anisaldehyde (0.61 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.61 g (yield 71%) of colorless powdery crystals (m.p.=291° C. (decomposed)).

Synthesis Example 15
Synthesis of 6-(3,4-methylenedioxybenzylidenehydrazino)-9H-purine-2(3H)-one [10e: $R^2$=3,4-methylenedioxyphenyl]

6-Hydrazino-9H-purine-2(3H)-one [9] (0.5 g, 3.0 mmol) and piperonal (0.68 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.66 g (yield 73%) of colorless powdery crystals (m.p.=299° C. (decomposed)).

Synthesis Example 16
Synthesis of 6-p-hydroxybenzylidenehydrazino-9H-purine-2(3H)-one [10f: $R^2$=4-hydroxyphenyl]

6-Hydrazino-9H-purine-2(3H)-one [9] (0.5 g, 3.0 mmol) and p-hydroxybenzaldehyde (0.55 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.59 g (yield 72%) of colorless powdery crystals (m.p.=299° C. (decomposed)).

Synthesis Example 17
Synthesis of 6-p-chlorobenzylidenehydrazino-9H-purine-2(3H)-one [10g: $R^2$=4-chlorophenyl]

6-Hydrazino-9H-purine-2(3H)-one [9] (0.5 g, 3.0 mmol) and p-chlorobenzaldehyde (0.63 g, 4.5 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.62 g (yield 76%) of colorless powdery crystals (m.p.=299° C. (decomposed)).

$^1$H-NMR (60 MHz, DMSO-$d_6$) δ: 7.52 (2H, d, $J_{A,B}$=8.52 Hz, Ar-mH), 8.07 (2H, d, $J_{A,B}$=8.52 Hz, Ar-oH), 8.62 (1H, s, 8-H), 8.67 (1H, s, N=CH)

Purine compounds of 17a through 17e were synthesized in accordance with the following reaction scheme:

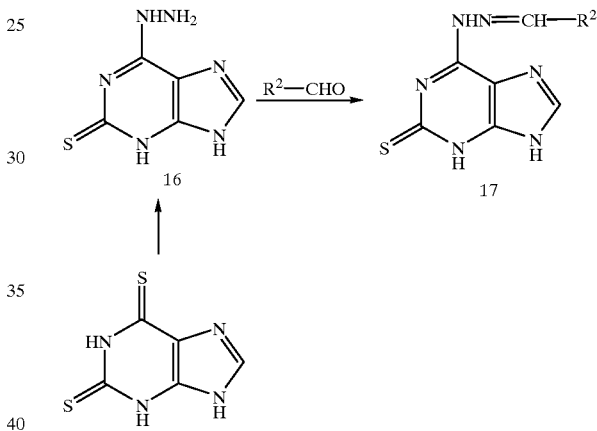

(wherein $R^2$ has the same meaning as defined above).

Synthesis Example 18
Synthesis of 6-p-fluorobenzylidenehydrazino-9H-purine-2(3H)-thione [17a: $R^2$=4-fluorophenyl]

(1) Synthesis of 6-hydrazino-9H-purine-2(3H)-thione [16]

2,6-Dithioxo-1,2,3,6-tetrahydro-9H-purine (0.5 g, 2.7 mmol) was added to 80% hydrazine hydrate (5 ml), and the mixture was stirred with heat for 10 minutes at 120° C. After completion of reaction, crystals that precipitated were collected by filtration, and washed with water. The crystals were recrystallized from water to obtain 0.30 g (yield 61%) of colorless powdery crystals (m.p.=292° C. (decomposed)).

$^1$H-NMR (60 MHz, DMSO-$d_6$) δ: 6.60 (2H, b r, exchangeable with $D_2O$, $NH_2$), 8.03 (1H, s, 8-H)

(2) Synthesis of 6-p-fluorobenzylidenehydrazino-9H-purine-2(3H)-thione [17a: $R^2$=4-fluorophenyl]

6-Hydrazino-9H-purine-2(3H)-thione [16] (0.5 g, 2.7 mmol) and p-fluorobenzaldehyde (0.51 g, 4.1 mmol) were added to acetic acid (30 ml), and the mixture was stirred for 4 hours at room temperature. After completion of reaction, crystals that precipitated were collected by filtration, and washed with ethanol. The crystals were recrystallized from DMF to obtain 0.48 g (yield 61%) of colorless powdery crystals (m.p.=286° C. (decomposed)).

Synthesis Example 19

Synthesis of 6-p-N,N-dimethylaminobenzylidenehydrazino-9H-purine-2(3H)-thione [17b: $R^2$=4-dimethylaminophenyl]

6-Hydrazino-9H-purine-2(3H)-thione [16] (0.5 g, 2.7 mmol) and p-dimethylaminobenzaldehyde (0.61 g, 4.1 mmol) were added to acetic acid (30 ml), and the mixture was stirred for 4 hours at room temperature. After completion of reaction, crystals that precipitated were collected by filtration, and washed with ethanol. The crystals were recrystallized from DMF to obtain 0.57 g (yield 66%) of yellow powdery crystals (m.p.=283° C. (decomposed)).

Synthesis Example 20

Synthesis of 6-p-nitrobenzylidenehydrazino-9H-purine-2(3H)-thione [17c: $R^2$=4-nitrophenyl]

6-Hydrazino-9H-purine-2(3H)-thione [16] (0.5 g, 2.7 mmol) and p-nitrobenzaldehyde (0.62 g, 4.1 mmol) were added to acetic acid (30 ml), and the mixture was stirred for 4 hours at room temperature. After completion of reaction, crystals that precipitated were collected by filtration, and washed with ethanol. The crystals were recrystallized from DMF to obtain 0.51 g (yield 51%) of light-brown powdery crystals (m.p.=252° C. (decomposed)).

Synthesis Example 21

Synthesis of 6-p-methoxybenzylidenehydrazino-9H-purine-2(3H)-thione [17d: $R^2$=4-methoxyphenyl]

6-Hydrazino-9H-purine-2(3H)-thione [16] (0.5 g, 2.7 mmol) and p-anisaldehyde (0.56 g, 4.1 mmol) were added to acetic acid (30 ml), and the mixture was stirred for 4 hours at room temperature. After completion of reaction, crystals that precipitated were collected by filtration, and washed with ethanol. The crystals were recrystallized from DMF to obtain 0.49 g (yield 60%) of yellow powdery crystals (m.p.=268° C. (decomposed)).

Synthesis Example 22

Synthesis of 6-(3,4-methylenedioxybenzylidenehydrazino)-9H-purine-2(3H)-thione [17e: $R^2$=3,4-methylenedioxyphenyl]

6-Hydrazino-9H-purine-2(3H)-thione [16] (0.5 g, 2.7 mmol) and piperonal (0.62 g, 4.1 mmol) were added to acetic acid (30 ml), and the mixture was stirred for 4 hours at room temperature. After completion of reaction, crystals that precipitated were collected by filtration, and washed with ethanol. The crystals were recrystallized from DMF to obtain 0.51 g (yield 59%) of yellow powdery crystals (m.p.=289° C. (decomposed)).

Purine compounds of 14a through 14e were synthesized in accordance with the following reaction scheme:

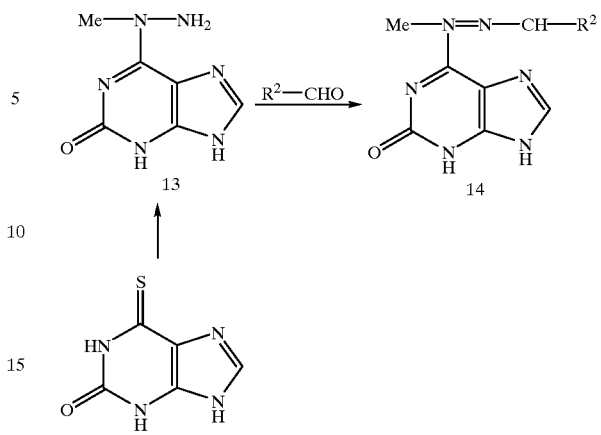

(wherein $R^2$ has the same meaning as defined above).

Synthesis Example 23

Synthesis of 6-[2-(2-methoxybenzylidene)-1-methylhydrazino]-9H-purine-2(3H)-one [14a: $R^2$=2-methoxyphenyl]

(1) Synthesis of 6-(1-methylhydrazino)-9H-purine-2(3H)-one [13]

2-Oxo-6-thioxo-1,2,3,6-tetrahydro-9H-purine (1.0 g, 5.9 mmol) were added to methylhydrazine (20 ml), and the mixture was stirred in a sealed tube for 30 minutes at 120° C. After completion of reaction, the mixture was concentrated under reduced pressure. The residual crystals were washed with 50% ethanol, and crystals collected by filtration were recrystallized from ethanol to obtain 0.64 g (yield 60%) of colorless powdery crystals (m.p.=247° C. (decomposed)).

$^1$H-NMR (60 MHz, TFA-d$_1$) δ: 3.88 (3H, s, NMe), 8.89 (1H, s, 8 -H)

(2) Synthesis of 6-[2-(2-methoxybenzylidene)-1-methylhydrazino]-9H-purine-2(3H)-one [14a: $R^2$=2-methoxyphenyl]

6-(1-Methylhydrazino)-9H-purine-2(3H)-one [13] (0.5 g, 2.8 mmol) and o-anisaldehyde (0.57 g, 4.2 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.54 g (yield 66%) of pale yellow powdery crystals (m.p.=271° C. (decomposed)).

Synthesis Example 24

Synthesis of 6-[2-(3-methoxybenzylidene)-1-methylhydrazino]-9H-purine-2(3H)-one [14b: $R^2$=3-methoxyphenyl]

6-(1-Methylhydrazino)-9H-purine-2(3H)-one [13] (0.5 g, 2.8 mmol) and m-anisaldehyde (0.57 g, 4.2 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.51 g (yield 62%) of pale yellow powdery crystals (m.p.=246° C. (decomposed)).

Synthesis Example 25
Synthesis of 6-[2-(4-methoxybenzylidene)-1-methylhydrazino]-9H-purine-2(3H)-one [14c: $R^2$=4-methoxyphenyl]

6-(1-Methylhydrazino)-9H-purine-2(3H)-one [13] (0.5 g, 2.8 mmol) and p-anisaldehyde (0.57 g, 4.2 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.61 g (yield 74%) of yellow powdery crystals (m.p.=281° C. (decomposed)).

Synthesis Example 26
Synthesis of 6-[2-(4-fluorobenzylidene)-1-methylhydrazino]-9H-purine-2(3H)-one [14d: $R^2$=4-fluorophenyl]

6-(1-Methylhydrazino)-9H-purine-2(3H)-one [13] (0.5 g, 2.8 mmol) and p-fluorobenzaldehyde (0.52 g, 4.2 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.57 g (yield 72%) of yellow needles (m.p.=241° C. (decomposed)).

Synthesis Example 27
Synthesis of 6-[2-(4-hydroxybenzylidene)-1-methylhydrazino]-9H-purine-2(3H)-one [14e: $R^2$=4-hydroxyphenyl]

6-(1-Methylhydrazino)-9H-purine-2(3H)-one [13] (0.5 g, 2.8 mmol) and p-hydroxybenzaldehyde (0.51 g, 4.2 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.55 g (yield 70%) of yellow powdery crystals (m.p.=265° C. (decomposed)).

Purine compounds of 19a and 19b were synthesized in accordance with the following reaction scheme:

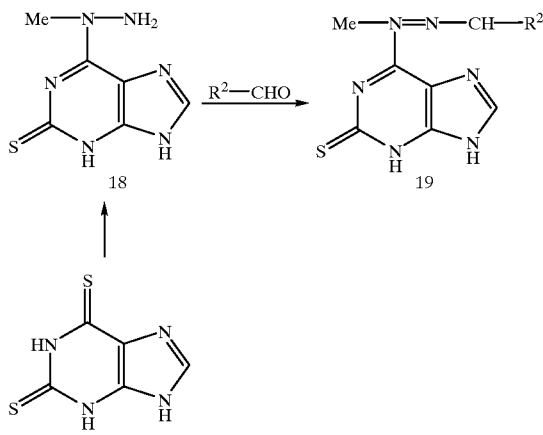

(wherein $R^2$ has the same meaning as defined above).

Synthesis Example 28
Synthesis of 6-[2-(4-methoxybenzylidene)-1-methylhydrazino]-9H-purine-2(3H)-thione [19a: $R^2$=4-methoxyphenyl]

(1) Synthesis of 6-(1-methylhydrazino)-9H-purine-2(3H)-thione [18]

2,6-Dioxo-1,2,3,6-tetrahydro-9H-purine (1.0 g, 5.4 mmol) was added to methylhydrazine (20 ml), and the mixture was stirred in a sealed tube for 30 minutes at 120° C. After completion of reaction, the mixture was concentrated under reduced pressure. The residual crystals were washed with 50% ethanol, and crystals collected by filtration were recrystallized from ethanol to obtain 0.60 g (yield 56%) of colorless powdery crystals (m.p.=245° C.).

$^1$H-NMR (60 MHz, DMSO-$d_6$) δ: 2.60 (3H, s, NMe), 3.95 (2H, br, exchangeable with $D_2O$, $NH_2$), 7.94 (1H, s, 8-H)

(2) Synthesis of 6-[2-(4-methoxybenzylidene)-1-methylhydrazino]-9H-purine-2(3H)-thione [19a: $R^2$=4-methoxyphenyl]

6-(1-Methylhydrazino)-9H-purine-2(3H)-thione [18] (0.5 g, 2.5 mmol) and p-anisaldehyde (0.52 g, 3.8 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.46 g (yield 57%) of pale yellow powdery crystals (m.p.=243° C. (decomposed)).

$^1$H-NMR (60 MHz, DMSO-$d_6$) δ: 3.76 (3H, s, NMe), 3.83 (3H, s, OMe), 6.85–7.25 (2H, m, Ar-H), 7.70–8.05 (2H, m, Ar-H), 8.18 (1H, s, N=CH), 8.33 (1H, s, 8-H)

Synthesis Example 29
Synthesis of 6-[2-(4-fluorobenzylidene)-1-methylhydrazino]-9H-purine-2(3H)-thione [19b: $R^2$=4-fluorophenyl]

6-(1-Methylhydrazino)-9H-purine-2(3H)-thione [18] (0.5 g, 2.5 mmol) and p-fluorobenzaldehyde (0.47 g, 3.8 mmol) were added to acetic acid (30 ml), and the mixture was stirred for 4 hours at room temperature. After completion of reaction, the solvent was evaporated under reduced pressure so as to precipitate solid crystals. The crystals were recrystallized from DMF to obtain 0.45 g (yield 59%) of pale yellow powdery crystals (m.p.=273° C. (decomposed)).

$^1$H-NMR (60 MHz, DMSO-$d_6$) δ: 2.58 (3H, s, NMe), 7.26 (2H, t, $J_{H,H}$=8.52 Hz, $J_{H,F}$=9.36 Hz, Ar-mH), 7.94 (2H, dd, $J_{H,H}$=8.52 Hz, $J_{H,F}$=5.58 Hz, Ar-oH), 8.01 (1H, s, N=CH), 8.14 (1H, s, 8-H)

The $^1$H-NMR spectrum data of the synthesized compounds are shown in the following Tables.

| Compound No. | $R^2$ | δ(DMSO-$d_6$, 60 MHz) |
|---|---|---|
| $^1$H NMR Spectrum data of 6-(alkylidene-hydrazino- or benzylidene-hydrazino)-2-chloro-9H-purine (3a–3i) | | |
| 3a | n-Pro | 0.95(3H, t, J=6.75Hz, N=CHCH$_2$CH$_2$CH$_3$), 1.26–1.84(2H, m, N=CHCH$_2$CH$_2$CH$_3$), 2.25–2.57(2H, m, N=CHCH$_2$CH$_2$CH$_3$), 7.51(1H, br t, J=6.15Hz, N=CH), 8.34 (1H s, 8-H), 11.74(1H, s, exchangeable with $D_2O$, NH), 12.2(1H, br s, exchangeable |

-continued

| Compound No. | $R^2$ | δ(DMSO-$d_6$, 60 MHz) |
|---|---|---|
| | | with $D_2O$, NH) |
| 3b | Ph | 7.33–7.66(3H, m, Ph—H), 7.73–8.13(2H, m, Ph—H), 8.27(1H, s, N=CH), 8.43(1H, s, 8-H), 12.15(2H, br s, exchangeable with $D_2O$, NH×2) |
| 3c | 4-F—$C_6H_4$ | 7.31(2H, t; $J_{H,H}$=8.76Hz, $J_{H,F}$=8.82Hz, Ar—mH), 7.99(2H, dd, $J_{H,H}$=8.76Hz,$J_{H,F}$=5.28Hz, Ar—oH), 8.25(1H, s, N=CH), 8.42 (1H, s, 8-H), 12.13(2H, br s, exchangeable with $D_2O$, NH×2) |
| 3d | 4-Cl—$C_6H_4$ | 7.51(2H, d, $J_{A,B}$=8.82Hz, Ar—mH), 7.94(2H, d, $J_{A,B}$=8.82Hz, Ar—oH), 8.25(1H, s, N=CH), 8.42(1H, s, 8-H), 12.16(2H, br s, exchangeable with $D_2O$, NH×2) |
| 3e | 4-MeO—$C_6H_4$ | 3.83(3H, s, OMe), 7.03(2H, d, $J_{A,B}$=8.76Hz, Ar—mH), 7.87(2H, d, $J_{A,B}$=8.76Hz, Ar—oH), 8.20(1H, s, N=CH), 8.38(1H, s, 8-H), 12.00(2H, s, exchangeable with $D_2O$, NH) |
| 3f | 4-Me$_2$N—$C_6H_4$ | 3.00(6H, s, NMe$_2$), 6.75(2H, d, $J_{A,B}$=8.76Hz, Ar—mH), 7.73(2H, d, $J_{A,B}$=8.76Hz, Ar—oH), 8.13(1H, s, N=CH), 8.35(1H, s, 8-H), 11.83(1H, s, exchangeable with $D_2O$, NH) |
| 3g | 3,4-$CH_2O_2$—$C_6H_3$ | 6.12(2H, s, OCH$_2$O), 6.97(1H, d, $J_{5',6'}$=8.22Hz, 5'-H), 7.21(1H, d, $J_{5',6'}$=8.22Hz, $J_{2',6'}$=1.80Hz, 6'-H), 7.80(1H, d, $J_{2',6'}$=1.80Hz, 2'-H), 8.15(1H, s, N=CH), 8.39 (1H, s, 8-H), 12.01(2H, s, exchangeable with $D_2O$, NH×2) |
| 3h | 4-O$_2$N—$C_6H_4$ | 8.07(2H, d, $J_{A,B}$=8.82Hz, Ar—oH), 8.46(2H, d, $J_{A,B}$=8.82Hz, Ar—mH), 8.54(1H, s, 8-H), 9.45(1H, s, N=CH) |
| 3i | 4-HO—$C_6H_4$ | 6.87(2H, d, $J_{A,B}$=8.22Hz, Ar—mH), 7.76(2H, d, $J_{A,B}$=8.22Hz, Ar—oH), 8.16(1H, s, N=CH), 8.37(1H, s, 8-H), 9.89(1H, s, exchangeable with $D_2O$, OH), 11.90(2H, s, exchangeable with $D_2O$, NH×2) |

$^1$H NMR Spectrum data of 6-benzylidene-hydrazino-9H-purine-2(3H)-one (10a–10f)

| | | |
|---|---|---|
| 10a | 4-F—$C_6H_4$ | 7.26(2H, t, $J_{H,H}$=8.52Hz, $J_{H,F}$=9.06Hz, Ar—mH), 7.83(1H, s, N=CH), 8.08(2H, dd, $J_{H,H}$=8.52Hz, $J_{H,F}$=5.58Hz, Ar—oH), 8.40 (1H, s, 8-H), 10.15, 11.20 and 11.70 (each 1H, each br, exchangeable with $D_2O$, NH×3) |
| 10b | 4-Me$_2$N—$C_6H_4$ | 2.99(6H, s, NMe$_2$), 6.73(2H, d, $J_{A,B}$=8.22Hz, Ar—mH), 7.77(2H, d, $J_{A,B}$=8.22Hz, Ar—oH),7.78(1H, s, N=CH), 8.28(1H, s, 8-H), 9.80, 10.50 and 11.24(each 1H, each br, exchangeable with $D_2O$, NH×3) |
| 10c* | 4-O$_2$N—$C_6H_4$ | 8.42(4H, s, Ar—H), 8.65(1H, s, 8-H), 8.79(1H, s, N=CH) |
| 10d | 4-MeO—$C_6H_4$ | 3.82(3H, s, OMe), 6.99(2H, d, $J_{A,B}$=8.22Hz, Ar—mH), 7.86(1H, s, N=CH), 7.92 (2H, d, $J_{A,B}$=8.22Hz, Ar—oH), 8.35 (1H, s, 8-H), 10.40–11.75(2H, br, exchangeable with $D_2O$, NH×2) |
| 10e | 3,4-$CH_2O_2$—$C_6H_3$ | 6.08(2H, s, OCH$_2$O), 6.94(1H, d, $J_{5',6'}$=7.62Hz, 5'-H), 7.27(1H, dd, $J_{5',6'}$=7.62Hz, $J_{2',6'}$=1.20Hz, 6'-H), 7.83(1H, d, $J_{2',6'}$=1.20Hz, 2'-H), 8.00(1H, s, N=CH), 8.30 (1H, s, 8-H), 10.25, 11.10 and 11.88(each 1H, each br, exchangeable with $D_2O$, NH×3) |
| 10f | 4-HO—$C_6H_4$ | 6.82(2H, d, $J_{A,B}$=7.92Hz, Ar—mH), 7.81 (1H, s, N=CH), 7.83(2H, d, $J_{A,B}$=7.92Hz, Ar—oH), 8.32(1H, s, 8-H), 9.80–11.60(3H, br, exchangeable with $D_2O$, NH×3) |

| Compound No. | $R^2$ | δ(DMSO-$d_6$, 60 MHz) |
|---|---|---|

$^1$H NMR Spectrum data of 6-benzylidene-hydrazino-9H-purine-2(3H)-thione (17a–17e)

| | | |
|---|---|---|
| 17a* | 4-F—$C_6H_4$ | 7.23(2H, t, $J_{H,H}$=8.52Hz, $J_{H,F}$=9.36Hz, Ar—mH), 8.07(2H, dd, $J_{H,H}$=8.52Hz, $J_{H,F}$=5.58Hz, Ar—oH), 8.66(1H, s, N=CH), 8.95 (1H, s, 8-H) |
| 17b* | 4-Me$_2$N—$C_6H_4$ | 3.54(6H, s, NMe$_2$), 7.81(2H, d, $J_{A,B}$=8.82Hz, Ar—mH), 8.32(2H, d, $J_{A,B}$=8.82Hz, Ar—oH), 8.63(1H, s, N=CH), 8.94(1H, s, 8-H) |
| 17c* | 4-O$_2$N—$C_6H_4$ | 8.24(2H, d, $J_{A,B}$=8.82Hz, Ar—mH), 8.47(2H, d, $J_{A,B}$=8.82Hz, Ar—oH), 8.64(1H, s, N=CH), 8.95(1H, s, 8-H) |
| 17d* | 4-MeO—$C_6H_4$ | 4.05(3H, s, OMe), 7.16(2H, d, $J_{A,B}$=8.76Hz, Ar—mH), 7.98(2H, d, $J_{A,B}$=8.76Hz, Ar—oH), 8.60(1H, s, N=CH), 8.96(1H, s, 8-H) |
| 17e* | 3,4-$CH_2O_2$—$C_6H_3$ | 6.12(2H, s, OCH$_2$O), 6.99(1H, d, $J_{5',6'}$=7.32Hz, 5'-H), 7.39(1H, dd, $J_{5',6'}$=7.32Hz, $J_{2',6'}$=1.20Hz, 6'-H), 7.60(1H, d, $J_{2',6'}$=1.20Hz, 2'-H), 8.55(1H, s, N=CH), 8.91 (1H, s, 8-H) |

$^1$H NMR Spectrum data of 6-(2-benzylidene-1-methylhydrazino)-9H-purine-2(3H)-one (14a–14e)

| | | |
|---|---|---|
| 14a* | 2-MeO—$C_6H_4$ | 4.03(3H, s, NMe), 4.25(3H, s, OMe), 7.10–7.82(4H, m, Ar—H), 8.61(1H, s, N=CH), 8.98(1H, s, 8-H) |
| 14b | 3-MeO—$C_6H_4$ | 3.70(3H, s, NMe), 3.84(3H, s, OMe), 6.90–7.60(4H, m Ar—H), 8.02(1H, s, N=CH, 8.22(1H, s, 8-H) |
| 14c | 4-MeO—$C_6H_4$ | 3.70(3H, s, NMe), 3.83(3H, s, OMe), 7.02(2H, $J_{A,B}$=8.22Hz, Ar—mH), 7.92 (2H, $J_{A,B}$=8.22Hz, Ar—oH), 8.20(1H, s N=CH), 8.35(1H, s, 8-H) |
| 14d | 4-F—$C_6H_4$ | 3.69(3H, s, NMe), 6.70–7.10(2H, m, Ar—H), 7.65–8.10(2H, m, Ar—H), 8.00 (1H, s, N=CH), 8.30(1H, s, 8-H) |
| 14e* | 4-HO—$C_6H_4$ | 4.02(3H, s, NMe), 6.95–7.30(2H, m, Ar—H), 7.70–8.05(2H, m, Ar—H), 8.58 (1H, s, N=CH), 8.81(1H, s, 8-H) |

*TFA-$d_1$, 60 MHz (Synthesis examples of triazolopurine compounds)

Triazolopurine compounds of 4a through 4e and 5d were synthesized in accordance with the following reaction scheme:

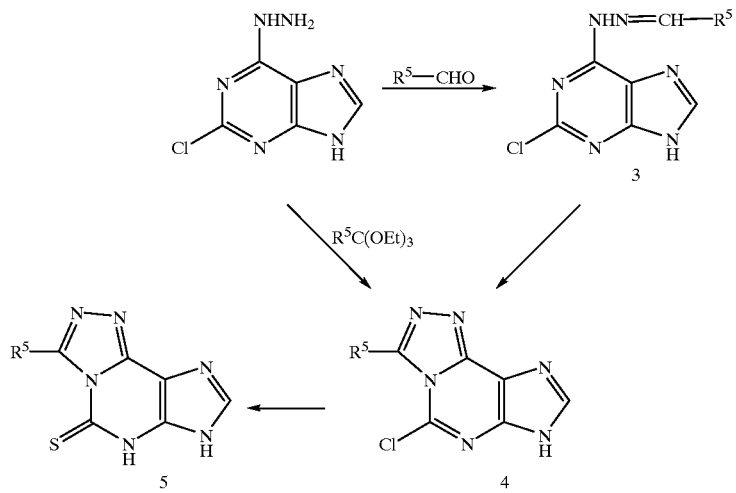

(wherein $R^5$ has the same meaning as defined above).

Synthesis Example 30

Synthesis of 5-chloro-7H-[1,2,4]triazolo[3,4-i]-purine [4a: $R^5$=hydrogen]

Trifluoroacetic acid (10 ml) was added to a mixture of 2-chloro-6-hydrazino-9H-purine (1.0 g, 5.4 mmol) and triethyl orthoformate (40 ml), and the resultant mixture was stirred for 3 hours at room temperature. After completion of reaction, the solid that precipitated was collected by filtration, recrystallized from water to obtain 0.50 g (yield 48%) of colorless powdery crystals (m.p.>300° C.).

Synthesis Example 31

Synthesis of 5-chloro-3-methyl-7H-[1,2,4]triazolo-[3,4-i]purine [4b: $R^5$=methyl]

Trifluoroacetic acid (5 ml) was added to a mixture of 2-chloro-6-hydrazino-9H-purine (1.0 g, 5.4 mmol) and triethyl orthoacetate (40 ml), and the resultant mixture was stirred for 3 hours at room temperature. After completion of reaction, the solid that precipitated was collected by filtration, recrystallized from water to obtain 0.5 g (yield 44%) of colorless powdery crystals (m.p.>300° C.).

Synthesis Example 32

Synthesis of 5-chloro-3-phenyl-7H-[1,2,4]triazolo-[3,4-i]purine [4c: $R^5$=phenyl]

6-Benzylidenehydrazino-2-chloro-9H-purine [3b] (1.0 g, 3.7 mmol) and lead tetraacetate (2.5 g, 5.6 mmol) were added to dioxane (30 ml), and the mixture was stirred for 2 hours at room temperature. After completion of reaction, water (100 ml) was added to the mixture, and extracts with cyclohexane (50 ml×3) were removed. The target substance was taken up from aqueous layers with ethyl acetate (50 ml×3). After the solvent for extraction was evaporated, the solid that precipitated was recrystallized from water to obtain 0.53 g (yield 54%) of colorless powdery crystals (m.p.>300° C.).

Synthesis Example 33

Synthesis of 5-chloro-3-p-fluorophenyl-7H-[1,2,4]triazolo[3,4-i]purine [4d: $R^5$=4-fluorophenyl]

2-Chloro-6-p-fluorobenzylidenehydrazino-9H-purine [3c] (1.0 g, 3.4 mmol) and lead tetraacetate (2.3 g, 5.1 mmol) were added to dioxane (30 ml), and the mixture was stirred for 2 hours at room temperature. After completion of reaction, water (100 ml) was added to the mixture, and extracts with cyclohexane (50 ml×3) were removed. The target substance was taken up from aqueous layers with ethyl acetate (50 ml×3). After the solvent for extraction was evaporated, the solid that precipitated was recrystallized from water to obtain 0.57 g (yield 58%) of colorless powdery crystals (m.p.>300° C.).

Synthesis Example 34

Synthesis of 5-chloro-3-p-methoxyphenyl-7H-[1,2,4]triazolo[3,4-i]purine [4e: $R^5$=4-methoxyphenyl]

2-Chloro-6-p-methoxybenzylidenehydrazino-9H-purine [3e] (1.0 g, 3.3 mmol) and lead tetraacetate (2.2 g, 5.0 mmol) were added to dioxane (30 ml), and the mixture was stirred for 2 hours at room temperature. After completion of reaction, water (100 ml) was added to the mixture, and extracts with cyclohexane (50 ml×3) were removed. The target substance was taken up from aqueous layers with ethyl acetate (50 ml×3). After the solvent for extraction was evaporated, the solid that precipitated was recrystallized from water to obtain 0.61 g (yield 62%) of colorless powdery crystals (m.p.>300° C.).

Synthesis Example 35

Synthesis of 3-p-methoxyphenyl-7H-[1,2,4]triazolo[3,4-i]purine-5(6H)-thione [5d: $R^5$=4-methoxyphenyl]

5-Chloro-3-p-methoxyphenyl-7H-[1,2,4]triazolo[3,4-i]purine [4e] (0.3 g, 1.0 mmol) and thiourea (0.15 g, 2.0 mmol) were added to ethanol (40 ml), and the mixture was heated under reflux for 10 hours. After completion of reaction, the crystals that precipitated were collected by filtration and recrystallized from DMF to obtain 0.21 g (yield 71%) of colorless powdery crystals (m.p.>281° C. (decomposed)).

Triazolopurine compounds of 8a through 8d were synthesized in accordance with the following reaction scheme:

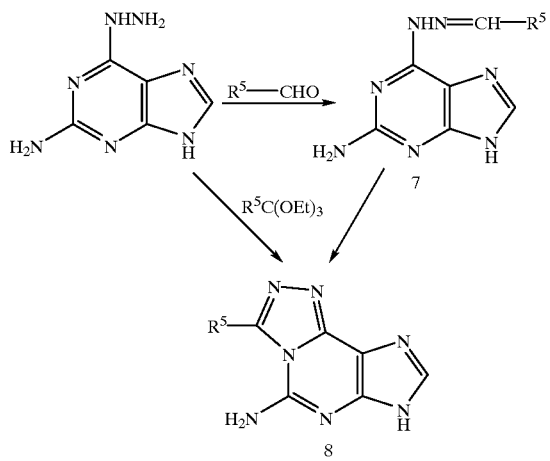

(wherein R⁵ has the same meaning as defined above).

Synthesis Example 36
Synthesis of 5-amino-7H-[1,2,4]triazolo[3,4-i]-purine [8a: R⁵=hydrogen]
2-Amino-6-hydrazino-9H-purine (1.0 g, 6.1 mmol) and triethyl orthoformate (9.0 g, 61.0 mmol) were added to DMF (5 ml), and the mixture was stirred for 5 hours at 150° C. After completion of reaction, the crystals that precipitated were collected by filtration, washed with ethanol, and recrystallized from DMF to obtain 0.64 g (yield 61%) of colorless powdery crystals (m.p.=280° C. (decomposed)).

Synthesis Example 37
Synthesis of 5-amino-3-methyl-7H-[1,2,4]-triazolo[3,4-i] purine [8b: R⁵=methyl]
2-Amino-6-hydrazino-9H-purine (1.0 g, 6.1 mmol) and triethyl orthoacetate (9.9 g, 61.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.76 g (yield 66%) of colorless powdery crystals (m.p. =274° C. (decomposed)).

Synthesis Example 38
Synthesis of 5-amino-3-phenyl-7H-[1,2,4]-triazolo[3,4-i] purine [8c: R⁵=phenyl]
2-Amino-6-hydrazino-9H-purine (1.0 g, 6.1 mmol) and triethyl orthobenzoate (9.0 g, 40.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.91 g (yield 60a) of colorless powdery crystals (m.p.>300° C.).

Synthesis Example 39
Synthesis of 5-amino-3-p-methoxyphenyl-7H-[1,2,4]-triazolo[3,4-i]purine [8d: R⁵=4-methoxyphenyl]
2-Amino-6-p-methoxybenzylidenehydrazino-9H-purine [7] (0.5 g, 1.8 mmol) and lead tetraacetate (1.2 g, 2.7 mmol) were added to acetic acid (30 ml), and the mixture was stirred for 5 hours at 120° C. After completion of reaction, the solid matter was removed, followed by concentration under reduced pressure. The residue was purified by use of columns (Merck kiesel gel 60: ethyl acetate and ethanol) and recrystallized from water to obtain 0.23 g (yield 46%) of pale yellow powdery crystals (m.p.=225° C. (decomposed)).

Triazolopurine compounds of 11a through 11e were synthesized in accordance with the following reaction scheme:

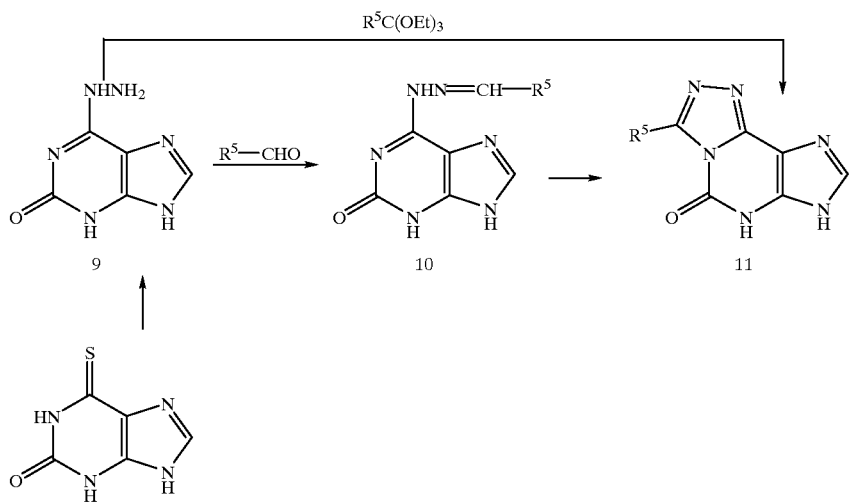

(wherein R⁵ has the same meaning as defined above).

Synthesis Example 40

Synthesis of 7H-[1,2,4]triazolo[3,4-i]purine-5(6H)-one [11a: R⁵=hydrogen]

6-Hydrazino-9H-purine-2(3H)-one [9] (1.0 g, 6.0 mmol) and triethyl orthoformate (8.9 g, 60.0 mmol) were added to DMF (5 ml), and the mixture was stirred for 5 hours at 150° C. After completion of reaction, the crystals that precipitated were collected by filtration, washed with ethanol, and recrystallized from DMF to obtain 0.65 g (yield 61%) of colorless powdery crystals (m.p.=262° C. (decomposed)).

Synthesis Example 41
Synthesis of 3-methyl-7H-[1,2,4]triazolo[3,4-i]purine-5(6H)-one [11b: $R^5$=methyl]

6-Hydrazino-9H-purine-2(3H)-one [9] (1.0 g, 6.0 mmol) and triethyl orthoacetate (9.7 g, 60.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.66 g (yield 58%) of colorless powdery crystals (m.p.=277° C. (decomposed)).

Synthesis Example 42
Synthesis of 3-phenyl-7H-[1,2,4]triazolo[3,4-i]purine-5(6H)-one [11c: $R^5$=phenyl]

6-Hydrazino-9H-purine-2(3H)-one [9] (1.0 g, 6.0 mmol) and triethyl orthobenzoate (9.0 g, 40.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.87 g (yield 57%) of colorless powdery crystals (m.p.>300° C.).

Synthesis Example 43
Synthesis of 3-p-methoxyphenyl-7H-[1,2,4]triazolo[3,4-i]purine-5(6H)-one [11d: $R^5$=4-methoxyphenyl]

6-p-Methoxybenzylidenehydrazino-9H-purine-2(3H)-one [10d] (0.5 g, 1.76 mmol) and lead tetraacetate (1.17 g, 2.64 mmol) were added to dioxane (30 ml), and the mixture was stirred for 4 hours at 120° C. After completion of reaction, the solid matter was removed, followed by concentration under reduced pressure. The residue was purified by use of columns (Merck kiesel gel 60: ethyl acetate and ethanol) and recrystallized from water to obtain 0.28 g (yield 56%) of pale yellow powdery crystals (m.p.=174–175° C.).

Synthesis Example 44
Synthesis of 3-p-chlorophenyl-7H-[1,2,4]triazolo[3,4-i]purine-5(6H)-one [11e: $R^5$=4-chlorophenyl]

6-p-Chlorobenzylidenehydrazino-9H-purine-2(3H)-one [10g] (0.5 g, 1.85 mmol) and lead tetraacetate (1.17 g, 2.64 mmol) were added to dioxane (30 ml), and the mixture was stirred for 4 hours at 120° C. After completion of reaction, the solid matter was removed, followed by concentration under reduced pressure. The residue was purified by use of columns (Merck kiesel gel 60: ethyl acetate and ethanol) and recrystallized from water to obtain 0.28 g (yield 53%) of pale yellow powdery crystals (m.p.=230° C. (decomposed)).

$^1$H-NMR (60 MHz, DMSO-$d_6$) δ: 7.60 (2H, d, $J_{A,B}$=8.82 Hz, Ar-mH), 8.0 8 (2H, d, $J_{A,B}$=8.82 Hz, Ar-oH), 8.66 (1H, s, 8-H)

Triazolopurine compounds of 5a through 5d were synthesized in accordance with the following reaction scheme:

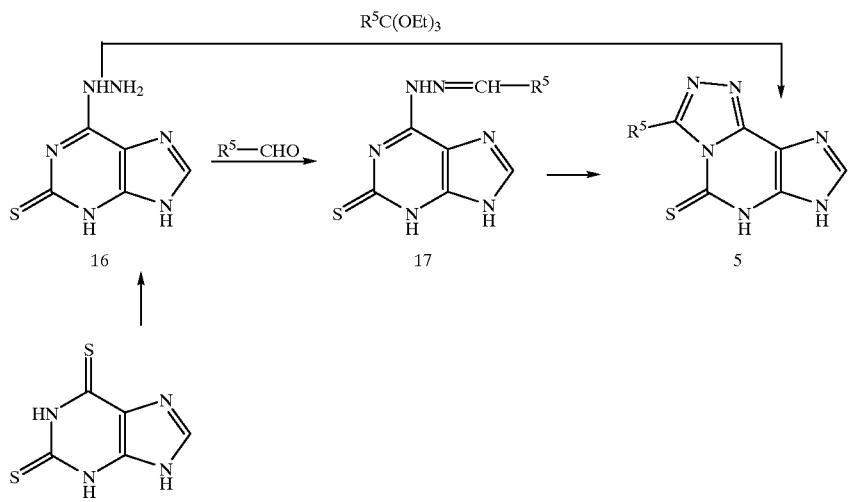

(wherein $R^5$ has the same meaning as defined above).

Synthesis Example 45
Synthesis of 7H-[1,2,4]triazolo[3,4-i]purine-5(6H)-thione [5a: $R^5$=hydrogen]

6-Hydrazino-9H-purine-2(3H)-thione [16] (1.0 g, 5.5 mmol) and triethyl orthoformate (8.1 g, 55.0 mmol) were added to DMF (5 ml), and the mixture was stirred for 5 hours at 150° C. After completion of reaction, the crystals that precipitated were collected by filtration, washed with ethanol, and recrystallized from DMF to obtain 0.66 g (yield 63%) of colorless powdery crystals (m.p.=271° C. (decomposed)).

Synthesis Example 46
Synthesis of 3-methyl-7H-[1,2,4]triazolo[3,4-i]purine-5(6H)-thione [5b: $R^5$=methyl]

6-Hydrazino-9H-purine-2(3H)-thione [16] (1.0 g, 5.5 mmol) and triethyl orthoacetate (8.9 g, 55.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.68 g (yield 60%) of pale yellow powdery crystals (m.p.=266° C. (decomposed)).

Synthesis Example 47

Synthesis of 3-phenyl-7H-[1,2,4]triazolo[3,4-i]purine-5(6H)-thione [5c: $R^5$=phenyl]

6-Hydrazino-9H-purine-2(3H)-thione [16] (1.0 g, 5.5 mmol) and triethyl orthobenzoate (9.0 g, 40.0 mmol) were added to DMF (5 ml), and the mixture was stirred for 5 hours at 160° C. After completion of reaction, the crystals that precipitated were collected by filtration, washed with ethanol, and recrystallized from DMF to obtain 0.86 g (yield 58%) of pale yellow powdery crystals (m.p.=251° C. (decomposed)).

Synthesis Example 48

Synthesis of 3-p-methoxyphenyl-7H-[1,2,4]triazolo[3,4-i]purine-5(6H)-thione [5d: $R^5$=4-methoxyphenyl]

6-p-Methoxybenzylidenehydrazino-9H-purine-2(3H)-thione [17d] (0.5 g, 1.66 mmol) and lead tetraacetate (1.10 g, 2.49 mmol) were added to dioxane (30 ml), and the mixture was stirred for 4 hours at 120° C. After completion of reaction, the solid matter was removed, followed by concentration under reduced pressure. The residue was purified by use of columns (Merck kieselgel 60: ethyl acetate and ethanol) and recrystallized from DMF to obtain 0.30 g (yield 60%) of colorless powdery crystals (m.p.>281° C. (decomposed)).

The 1H-NMR spectrum data of the synthesized compounds are shown in the following Tables.

| Compound No. | $R^5$ | δ(DMSO-$d_6$, 60 MHz) |
|---|---|---|
| $^1$H NMR Spectrum data of 3-alkyl-or 3-allyl-5-chloro-7H-[1,2,4]triazolo[3,4-i]purine (4a–4e) | | 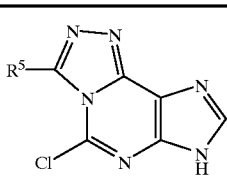 |
| 4a | H | 8.39(1H, s, 8-H), 9.51(1H, s, 3H) |
| 4b | $CH_3$ | 2.97(3H, s, Me), 8.33(1H, s, 8-H) |
| 4c | Ph | 7.50–7.76(5H, m, Ph—H), 8.41(1H, s, 8-H) |
| 4d | 4-F—$C_6H_4$ | 7.39(2H, dd, $J_{H,H}$=8.76Hz, $J_{H,F}$=8.82Hz, Ar—mH), 7.79(2H, dd, $J_{H,H}$=8.76Hz, $J_{H,F}$=5.28Hz, Ar—oH), 8.42(1H, s, 8-H) |
| 4e | 4-MeO—$C_6H_4$ | 3.86(3H, s, OMe), 7.09(2H, d, $J_{A,B}$=8.76Hz, Ar—mH), 7.63(2H, d, $J_{A,B}$=8.76Hz, Ar—oH), 8.40(1H, s, 8-H) |
| $^1$H NMR Spectrum data of 3-alkyl-or 3-allyl-5-amino-7H-[1,2,4]triazolo[3,4-i]purine (8a–8d) | | 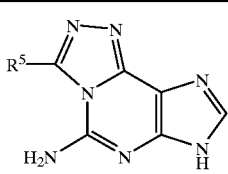 |
| 8a* | H | 8.94(1H, s, 8-H), 9.67(1H, s, 3-H) |
| 8b* | Me | 2.64(3H, s, Me), 8.93(1H, s, 8-H) |
| 8c* | Ph | 7.63–7.87(3H, m, Ph—H), 8.15–8.38(2H, m, Ph—H), 8.94(1H, s, 8-H) |
| 8d | 4-MeO—$C_6H_4$ | 3.86(3H, s, OMe), 7.12(2H, d, $J_{A,B}$=8.76Hz, Ar—mH), 7.58(2H, br s, exchangeable with $D_2O$, $NH_2$), 8.22(2H, d, $J_{A,B}$=8.76Hz, Ar—oH), 8.47(1H, s, 8-H) |

| Compound No. | $R^5$ | δ(DMSO-$d_6$, 60 MHz) |
|---|---|---|
| $^1$H NMR Spectrum data of 3-alkyl- or 3-allyl-7H-[1,2,4]triazolo[3,4-i]purine-5(6H)-one (11a–11d) | | |
| 11a | H | 8.10(1H, s, 8-H), 8.36(1H, s, 3-H), 12.20 (2H, br, exchangeable with $D_2O$, NH×2) |
| 11b* | Me | 2.83(3H, s, Me), 8.98(1H, s, 8-H) |
| 11c | Ph | 7.40–7.75(3H, m, Ph—H), 8.00–8.35(2H, m, Ph—H), 8.13(1H, s, 8-H) |
| 11d | 4-MeO—$C_6H_4$ | 3.83(3H, s, OMe), 7.05(2H, d, $J_{A,B}$=8.76Hz, Ar—mH), 7.82(2H, d, $J_{A,B}$=8.76Hz, Ar—oH), 8.62(1H, s, 8-H) |
| $^1$H NMR Spectrum data of 3-alkyl- or 3-allyl-7H-[1,2,4]triazolo[3,4-i]purine-5(6H)-one (5a–5d) | | |
| 5a | H | 8.37(1H, s, 8-H), 8.58(1H, s, 3-H) |
| 5b* | Me | 2.79(3H, s, Me), 8.96(1H, s, 8-H) |
| 5c | Ph | 7.40–7.80(3H, m, Ph—H), 8.05–8.35(2H, m, Ph—H), 8.30(1H, s, 8-H), 9.00(2H, br, exchangeable with $D_2O$, NH×2) |
| 5d | 4-MeO—$C_6H_4$ | 3.89(3H, s, OMe), 7.13(2H, d, $J_{A,B}$=8.76Hz, Ar—mH), 8.11(2H, d, $J_{A,B}$=8.76Hz, Ar—oH), 8.36(1H, s, 8-H) |

*TFA-$d_1$, 60 MHz

Test Example: Xanthine oxidase inhibitory activity

Xanthine (100 μM), bovine-milk-derived xanthine oxidase (XOD) (10 mU/ml), and a test compound were mixed in 50 mM phosphate buffer (pH 7.4), and the mixture was incubated for 15 minutes at room temperature. Transformation of xanthine into uric acid was measured as the change in absorbance (O.D.) at 292 nm, to thereby investigate the inhibitory effect of the test compound against uricogenesis.

The inhibition ratio against uricogenesis was calculated from the following equation, and a dose-response curve of each compound was obtained. From the curve, 50% inhibition coefficients ($IC_{50}$, μM) were computed. The control compound was allopurinol.

Inhibition ratio against uricogenesis (%)=100-[(D-$D_B$)/T]×100

T: O.D. of a solution of "xanthine+XOD"
D: O.D. of a solution of "test compound+xanthine+XOD"
DB: O.D. of a solution of "test compound+XOD"

The test results are shown in the Table below.

| Purine cmpd. No. | $IC_{50}$ (μM) | Purine cmpd. No. | $IC_{50}$ (μM) |
|---|---|---|---|
| 3b | 2.710 | 11c | 2.570 |
| 3c | 1.960 | 14a | 0.079 |
| 3d | 0.927 | 14b | 0.100 |
| 3e | 0.801 | 14c | 0.076 |
| 3f | 2.324 | 14d | 0.116 |
| 3g | 1.149 | 14e | 0.093 |
| 3i | 0.764 | 17a | 0.336 |

-continued

| | | | |
|---|---|---|---|
| 5b | 7.907 | 17b | 0.865 |
| 5c | 2.949 | 17c | 1.184 |
| 5d | 3.016 | 17d | 0.969 |
| 10a | 0.038 | 17e | 0.235 |
| 10b | 0.075 | 19a | 0.681 |
| 10c | 0.045 | 19b | 0.667 |
| 10d | 0.057 | | |
| 10e | 0.063 | | |
| 10f | 0.045 | | |
| 10g | 0.025 | | |

| | Control: Allopurinol > 10 |
|---|---|
| Triazolopurine Compound No. | IC$_{50}$ ($\mu$M) |
| 5b | 7.907 |
| 5c | 2.949 |
| 5d | 3.016 |
| 11c | 2.570 |
| 11e | 0.156 |

| | Control: Allopurinol > 10 |
|---|---|
| Formulation Example 1: Tablets | |
| Compound of the present invention | 30.0 mg |
| Microcrystalline cellulose | 25.0 mg |
| Lactose | 39.5 mg |
| Starch | 40.0 mg |
| Talc | 5.0 mg |
| Magnesium stearate | 0.5 mg |

Tablets having the above composition are prepared in accordance with a customary method.

| Formulation Example 2: Capsules | |
|---|---|
| Compound of the present invention | 30.0 mg |
| Lactose | 40.0 mg |
| Starch | 15.0 mg |
| Talc | 5.0 mg |

Capsules having the above composition are prepared in accordance with a customary method.

| Formulation Example 3: Injection preparation | |
|---|---|
| Compound of the present invention | 30.0 mg |
| Glucose | 100.0 mg |

The above ingredients are dissolved in purified water for injection use, to thereby prepare an injection preparation.

Industrial Applicability

The purine compounds and triazolopurine compounds of the present invention are endowed with an excellent xanthine oxidase inhibitory effect, and thus are useful as remedies for hyperuricemia, as well as preventive and therapeutic agents for gouty attacks.

We claim:
1. A purine compound of the following formula (I)

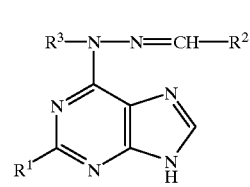

(wherein $R^1$ represents a hydrogen atom, a halogen atom, a hydroxyl group, a mercapto group, or an amino group; $R^2$ represents an alkyl group or an aryl group; and $R^3$ represents a hydrogen atom, an alkyl group, or an aryl group, provided that the case in which $R^1$ is a hydrogen atom, $R^2$ is a phenyl group, and $R^3$ is a methyl group is excluded.

2. The compound according to claim 1, wherein $R^1$ is a hydroxyl group.

3. The compound according to claim 1, wherein $R^1$ is a mercapto group.

4. The compound according to claim 1, wherein $R^2$ is an aryl group.

5. The compound according to claim 1, wherein $R^3$ is an alkyl group.

6. The compound according to claim 1, wherein $R^3$ is an aryl group.

7. The compound according to claim 1, wherein $R^1$ is a hydroxyl group, $R^2$ is an aryl group, and $R^3$ is an alkyl group.

8. The compound according to claim 1, wherein $R^1$ is a mercapto group, $R^2$ is an aryl group, and $R^3$ is an alkyl group.

9. The compound according to claim 1, wherein $R^1$ is a hydroxyl group, and $R^2$ and $R^3$ are aryl groups.

10. The compound according to claim 1, wherein $R^1$ is a mercapto group, and $R^2$ and $R^3$ are aryl groups.

11. A triazolopurine compound of the following formula (II)

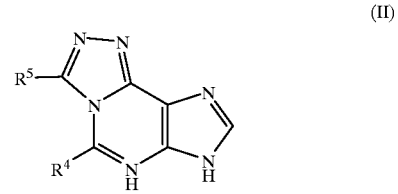

wherein $R^4$ represents a hydrogen atom, a halogen atom, a hydroxyl group, a mercapto group, or an amino group; and $R^5$ represents a hydrogen atom, an alkyl group, or an aryl group, excluding the compounds where $R^4$ is a hydrogen atom or a mercapto group and $R^5$ is a hydrogen atom.

12. The compound according to claim 11, wherein $R^4$ is a hydroxyl group.

13. The compound according to claim 11, wherein $R^5$ is an aryl group.

14. The compound according to claim 11, wherein $R^4$ is a hydroxyl group, and $R^5$ is an aryl group.

15. A pharmaceutical composition comprising as an active ingredient the compound of claim 1 or 11 and a pharmacologically acceptable carrier.

16. A method for the prevention or treatment of hyperuricemia or gout, which comprises administering an effective amount of a compound of formula (I) or (II) to a subject in need of such prevention or treatment,

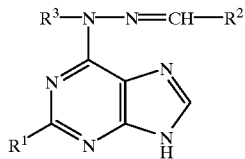
(I)

wherein $R^1$ represents a hydrogen atom, a halogen atom, a hydroxyl group, a mercapto group, or an amino group; $R^2$ represents an alkyl group or an aryl group; and $R^3$ represents a hydrogen atom, an alkyl group, or an aryl group,

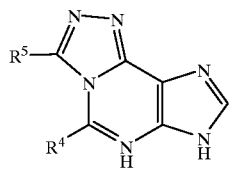
(II)

wherein $R^4$ represents a hydrogen atom, a halogen atom, a hydroxyl group, a mercapto group, or an amino group; and $R^5$ represents a hydrogen atom, an alkyl group, or an aryl group.

17. A method of inhibiting xanthine oxidase, which comprises administering an effective amount of a compound of formula (I) or (II) to a subject in need of xanthine oxidase inhibition,

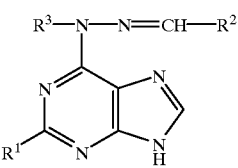
(I)

wherein $R^1$ represents a hydrogen atom, a halogen atom, a hydroxyl group, a mercapto group, or an amino group; $R^2$ represents an alkyl group or an aryl group; and $R^3$ represents a hydrogen atom, an alkyl group, or an aryl group,

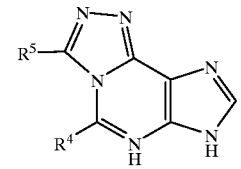
(II)

wherein $R^4$ represents a hydrogen atom, a halogen atom, a hydroxyl group, a mercapto group, or an amino group; and $R^5$ represents a hydrogen atom, an alkyl group, or an aryl group.

* * * * *